US012758711B2

(12) United States Patent
Clapham et al.

(10) Patent No.: US 12,758,711 B2
(45) Date of Patent: Oct. 13, 2026

(54) INTEGRATED PACKAGE FOR ADMINISTRATION OF LYOPHILIZED MEDICINES

(71) Applicants: Andrew John Clapham, Hummelstown, PA (US); Charles Heldebrant, Arcadia, CA (US)

(72) Inventors: Andrew John Clapham, Hummelstown, PA (US); Charles Heldebrant, Arcadia, CA (US)

( * ) Notice: Subject to any disclaimer, the term of this patent is extended or adjusted under 35 U.S.C. 154(b) by 879 days.

(21) Appl. No.: 18/076,777

(22) Filed: Dec. 7, 2022

(65) Prior Publication Data

US 2023/0173178 A1 Jun. 8, 2023

Related U.S. Application Data

(60) Provisional application No. 63/286,832, filed on Dec. 7, 2021.

(51) Int. Cl.
*A61M 5/19* (2006.01)
*A61M 5/28* (2006.01)
*A61M 39/00* (2006.01)
*A61M 39/24* (2006.01)

(52) U.S. Cl.
CPC .............. *A61M 5/19* (2013.01); *A61M 5/282* (2013.01); *A61M 2039/0027* (2013.01); *A61M 2039/0036* (2013.01); *A61M 2039/2446* (2013.01)

(58) Field of Classification Search
CPC .................... A61M 5/19; A61M 5/282; A61M 2039/0027; A61M 2039/0036; A61M 2039/2446; A61M 2005/1787; A61M 2005/3128; A61M 2005/31598; A61M 5/2448; A61M 5/284; A61M 5/31596
See application file for complete search history.

(56) References Cited

U.S. PATENT DOCUMENTS

| | | | | |
|---|---|---|---|---|
| 2,636,493 A * | 4/1953 | Lockhart | B65D 25/082 | 604/204 |
| 2,680,440 A * | 6/1954 | Fox | A61M 5/284 | 604/200 |
| 3,351,058 A * | 11/1967 | Webb | A61M 5/284 | D24/117 |
| 3,411,503 A * | 11/1968 | Santomieri | A61M 5/284 | 222/105 |
| 3,736,933 A * | 6/1973 | Szabo | A61M 5/002 | 604/200 |
| 7,207,970 B2 * | 4/2007 | Hasegawa | A61J 1/1437 | 604/416 |
| 8,663,188 B2 * | 3/2014 | Genosar | A61M 5/288 | 604/411 |
| 8,806,842 B1 * | 8/2014 | Penn | B65D 75/5811 | 53/474 |
| 10,835,678 B2 * | 11/2020 | Koska | A61M 5/50 | |
| 2001/0047162 A1 * | 11/2001 | Yugari | A61M 5/282 | 206/219 |
| 2010/0256556 A1 * | 10/2010 | Cray, Jr. | A61P 35/00 | 604/93.01 |

* cited by examiner

*Primary Examiner* — Theodore J Stigell

(57) ABSTRACT

An auto-disable prefillable integrated package apparatus includes a first chamber, a second chamber, a connection configured to form a communicable channel between the first chamber and the second chamber, a frangible membrane configured to form a rupturable barrier within the connector that separates the first chamber and the second chamber, and a hub configured to be communicably coupled to the second chamber.

9 Claims, 4 Drawing Sheets

INTEGRATED PACKAGE FOR ADMINISTRATION OF LYOPHILIZED MEDICINES

CROSS REFERENCE TO RELATED APPLICATION

This application claims the benefit of U.S. Provisional Application Ser. No. 63/286,832, filed Dec. 7, 2021, the entirety of which is incorporated by reference herein.

BACKGROUND OF THE INVENTION

Technical Field

Aspects of embodiments of the present disclosure relate to the field of auto-disable prefillable injection systems. More specifically, aspects of embodiments of the present disclosure are directed to multi-chamber prefillable injection systems.

Description of the Related Art

Drug delivery system for intramuscular (IM) or subcutaneous injections are commonly performed with syringes. Healthcare and nonhealthcare workers alike can use it for delivering vaccines and other drugs. However, the use of the syringe has its limitations. Generally, syringes are reusable and may increase the chance of cross-contamination or abuse, the drug itself is accessible and may be prone to tampering, the correct dose is dependent on the experience and skill of the user, and there may be several preparation steps involved and may be exposed to errors.

Auto-disable prefillable injection systems may be simple, safe, user friendly, contain the right dose, ready-to-use, and less prone to user error. However, these systems have limitations. Auto-disable prefillable injection systems may not be able be used for medicines that have lyophilization to preserve the functionality and quality of the medicine and thus require refrigeration to maintain the drug product to remain in a stable state.

Therefore, to overcome the problems and limitations described above, there is a need for an auto-disable prefillable injection system that may be configured to contain lyophilized drug products for delivery.

Problems that are to be Solved by the Invention

As mentioned previously, currently available injection systems may require the user to have significant experience and skill to correctly dose the injections delivered by the injection system, have time-consuming procedures in place to reduce the chance of cross-contamination and tampering and/or reduce the number of steps involved to lower the chance for errors. In addition, the use of auto-disable prefillable injection systems may not be available for medicines that have been lyophilized to preserve the functionality and quality of the medicine and thus require refrigeration to maintain the drug product to remain in a stable state.

Means for Solving the Problem

Aspects of embodiments of the present disclosure may be directed to an integrated package for the administration of one or more drug components that may be used with prefilled lyophilized medicines. In some embodiments, the integrated package of the present disclosure may provide the benefits of an auto-disable prefillable injection system having two or more chambers separated by a frangible membrane that may be advantageously used with lyophilized medicines.

Effect of the Invention

As such, aspects of embodiments of the present disclosure may provide the benefits of auto-disable prefillable injection systems that offer lyophilized medicines and minimize the risk of contamination, tampering, and user error.

SUMMARY OF THE INVENTION

One or more embodiments of the present disclosure may be directed to auto-disable prefillable integrated packages.

An auto-disable prefillable integrated package apparatus includes a first chamber, a second chamber, a connection configured to form a communicable channel between the first chamber and the second chamber, a frangible membrane configured to form a rupturable barrier within the connector that separates the first chamber and the second chamber, and a hub configured to be communicably coupled to the second chamber.

The auto-disable prefillable integrated package apparatus may have the second chamber include a compressible inner volume.

The auto-disable prefillable integrated package apparatus may further include a valve configured to prevent fluid flow from the second chamber into the first chamber via the connector.

The auto-disable prefillable integrated package apparatus may further include a needle assembly configured to be communicatively coupled to the hub.

The auto-disable prefillable integrated package apparatus may further include a bonded periphery.

The auto-disable prefillable integrated package apparatus may have the frangible membrane configured to rupture when a mechanical force above a rupture threshold is applied by a user to the connector.

The auto-disable prefillable integrated package apparatus may have the hub include a port.

The auto-disable prefillable integrated package apparatus may have the valve include a disc valve.

The auto-disable prefillable integrated package apparatus may have the frangible membrane include a polymer compound.

A multi-chamber integrated package apparatus includes a first chamber, a second chamber, a third chamber, a first connector configured to form a communicable channel between the first chamber and the third chamber, a second connector configured to form a communicable channel between the second chamber and the third chamber, a first frangible membrane configured to form a rupturable barrier within the first connector separating the first chamber and the third chamber, a second frangible membrane configured to form a rupturable barrier within the second connector separating the second chamber and the third chamber, and a hub configured to be communicatively coupled to the third chamber.

The multi-chamber integrated package apparatus may have the third chamber be configured to have a compressible inner volume.

The multi-chamber integrated package apparatus may have the third chamber be configured to contain a lyophilized drug product.

The multi-chamber integrated package apparatus may have the first chamber be configured to contain a reconstitution solution.

The multi-chamber integrated package apparatus may have the second chamber be configured to contain a reconstitution solution.

The multi-chamber integrated package apparatus may further include a needle assembly configured to be communicably coupled to the hub.

The multi-chamber integrated package apparatus may have the first frangible membrane and the second frangible membrane be configured to rupture when a mechanical force above a rupture threshold is applied by a user to the corresponding one of the first connector and the second connector.

A syringe-type integrated package apparatus includes a cylindrical body having a first chamber and a second chamber separated by a frangible membrane, a plunger assembly, a hub communicably coupled to the second chamber, and a needle assembly configured to be communicably coupled to the hub.

The syringe-type integrated package apparatus may have the frangible membrane be configured to rupture when a mechanical force above a rupture threshold is applied by a user to the plunger assembly in a direction that presses the plunger assembly into the cylindrical body.

The syringe-type integrated package apparatus may have the first chamber be configured to contain a reconstitution solution.

The syringe-type integrated package apparatus may have the second chamber be configured to contain a lyophilized drug product.

BRIEF DESCRIPTION

The features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

DETAILED DESCRIPTION

Figure 1:
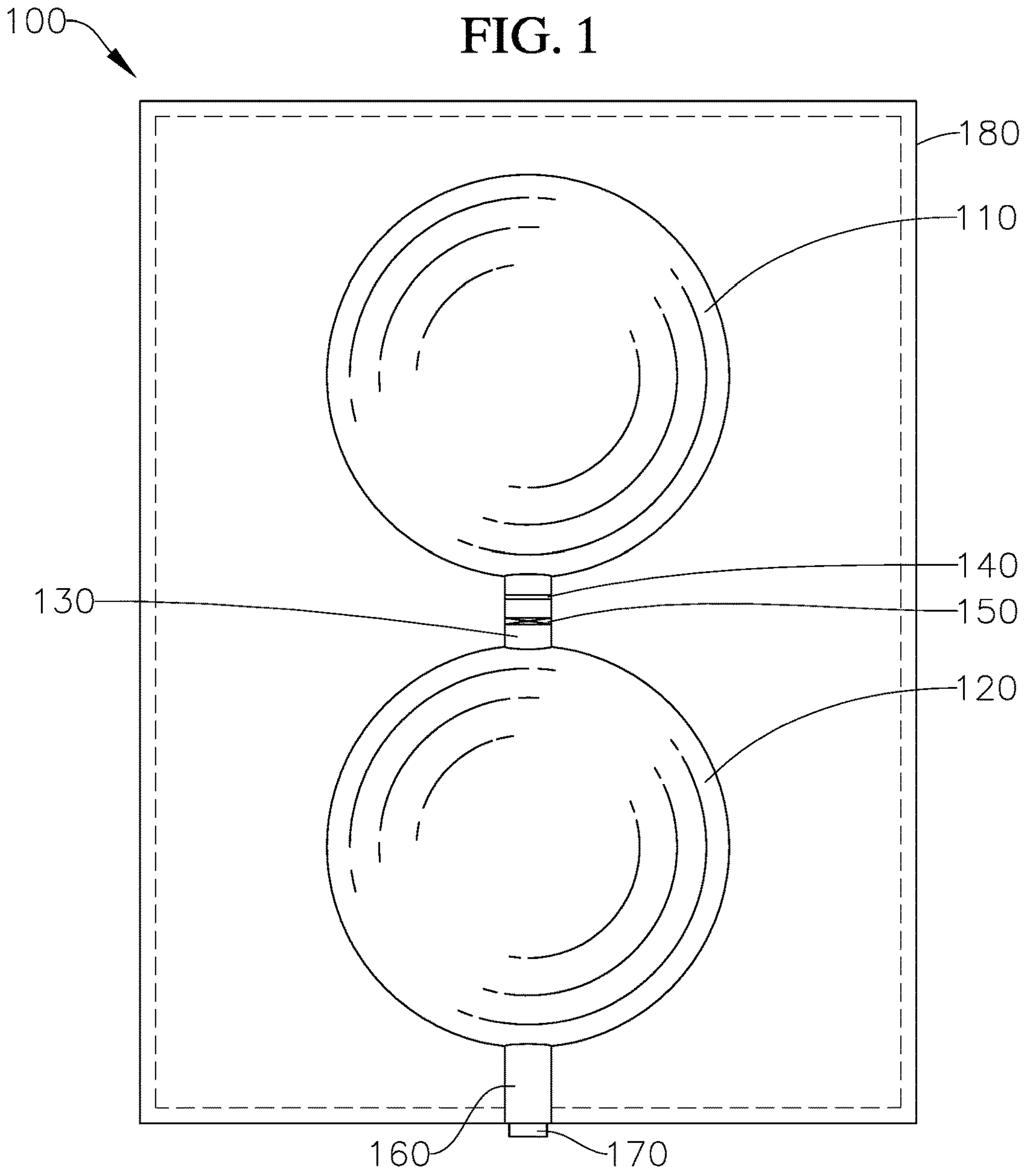
FIG. 1 is a diagram depicting an auto-disable prefillable integrated package having 2 chambers, according to aspects of embodiments of the present disclosure.

Features of the inventive concept and methods of accomplishing the same may be understood more readily by reference to the following detailed description of embodiments and the accompanying drawings. The inventive concept may, however, be embodied in many different forms and should not be construed as being limited to the embodiments set forth herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof will not be repeated. In the drawings, the relative sizes of elements, layers, and regions may be exaggerated for clarity.

It will be understood that, although the terms “first,” “second,” “third,” etc., may be used herein to describe various elements, components, regions, layers and/or sections, these elements, components, regions, layers and/or sections should not be limited by these terms. These terms are used to distinguish one element, component, region, layer or section from another element, component, region, layer, or section. Thus, a first element, component, region, layer, or section described below could be termed a second element, component, region, layer, or section, without departing from the spirit and scope of the present invention.

Spatially relative terms, such as “beneath,” “below,” “lower,” “under,” “above,” “upper,” and the like, may be used herein for ease of explanation to describe one element or feature’s relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as “below” or “beneath” or “under” other elements or features would then be oriented “above” the other elements or features. Thus, the example terms “below” and “under” can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being “on,” “connected to,” or “coupled to” another element or layer, it can be directly on, connected to, or coupled to the other element or layer, or one or more intervening elements or layers may be present. In addition, it will also be understood that when an element or layer is referred to as being “between” two elements or layers, it can be the only element or layer between the two elements or layers, or one or more intervening elements or layers may also be present.

The terminology used herein is for the purpose of describing particular embodiments only and is not intended to be limiting of the present invention. As used herein, the singular forms “a,” “an,” and “the” are intended to include the plural forms as well, unless the context clearly indicates otherwise. It will be further understood that the terms “comprises,” “comprising,” “includes,” and “including,” when used in this specification, specify the presence of the stated features, integers, steps, operations, elements, and/or components, but do not preclude the presence or addition of one or more other features, integers, steps, operations, elements, components, and/or groups thereof. As used herein, the term “and/or” includes any and all combinations of one or more of the associated listed items. Expressions such as “at least one of,” when preceding a list of elements, modify the entire list of elements and do not modify the individual elements of the list.

As used herein, the term “substantially,” “about,” and similar terms are used as terms of approximation and not as terms of degree, and are intended to account for the inherent deviations in measured or calculated values that would be recognized by those of ordinary skill in the art. Further, the use of “may” when describing embodiments of the present invention refers to “one or more embodiments of the present invention.” As used herein, the terms “use,” “using,” and “used” may be considered synonymous with the terms “utilize,” “utilizing,” and “utilized,” respectively. Also, the term “exemplary” is intended to refer to an example or illustration.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

For the purposes of this application, the words vaccine, organic material, food products, biologically active materials, antibiotics, proteins, or microorganism cultures may be understood to be interchangeable with each other, unless otherwise specified. Moreover, the words humans, animals, plants, and organisms may be interchangeable with each other, unless otherwise specified.

One or more embodiments according to the present disclosure will now be described. As described previously, drug delivery systems for intramuscular (IM) or subcutaneous injections are commonly performed with syringes. However, the use of the syringe has its limitations. Generally, syringes are reusable and may increase the chance of cross-contamination or abuse, the drug is accessible and may be prone to tampering, the correct dose is dependent on the experience and skill of the user, and there may be several preparation steps and may be prone to errors.

In addition, auto-disable prefillable injection systems may be simple, safe, user friendly, contain the right dose, ready-to-use, and less prone to user error. The system may contain a liquid or frozen drug product, sterile or otherwise, suitable for administration by injection, that may be ready for injection into a human, animal, or plant for administration of a liquid drug. However, these systems have limitations. Auto-disable prefillable injection systems may not be able to be used for medicines that have been prepared by lyophilization to preserve the functionality and quality of the medicine and thus require refrigeration to maintain the drug product to remain in a stable state. Moreover, similar single chamber systems may not be used for medicines that require lyophilization to preserve the functionality and quality of the medicine, and thus may require refrigeration to maintain the drug product so packaged in a stable state.

As such, aspects of embodiments of the present disclosure may provide an integrated package for the administration of lyophilized medicines or vaccines using an auto-disable prefillable injection apparatus that may, in some embodiments, have two or chambers separated by a frangible membrane that may keep the component compounds of the lyophilized medicine or vaccine separated until the components may be mixed just prior to administration.

Auto-Disable Prefillable Integrated Package

Figure 2:
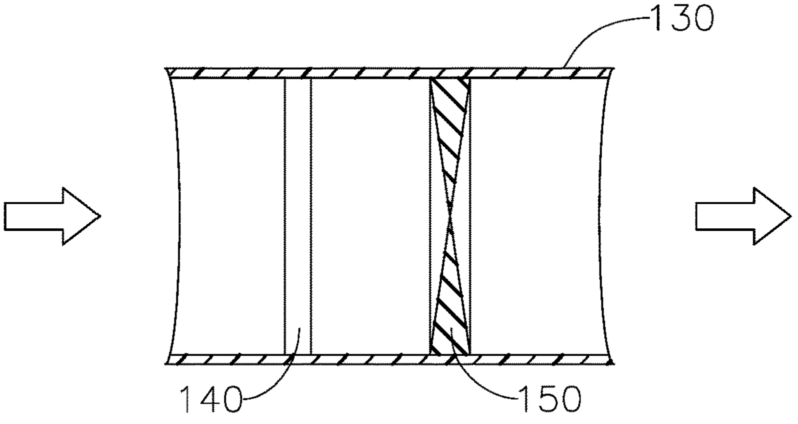
FIG. 2 is a cross-sectional view of a connector having a frangible membrane and a valve, according to aspects of embodiments of the present disclosure.
Figure 3:
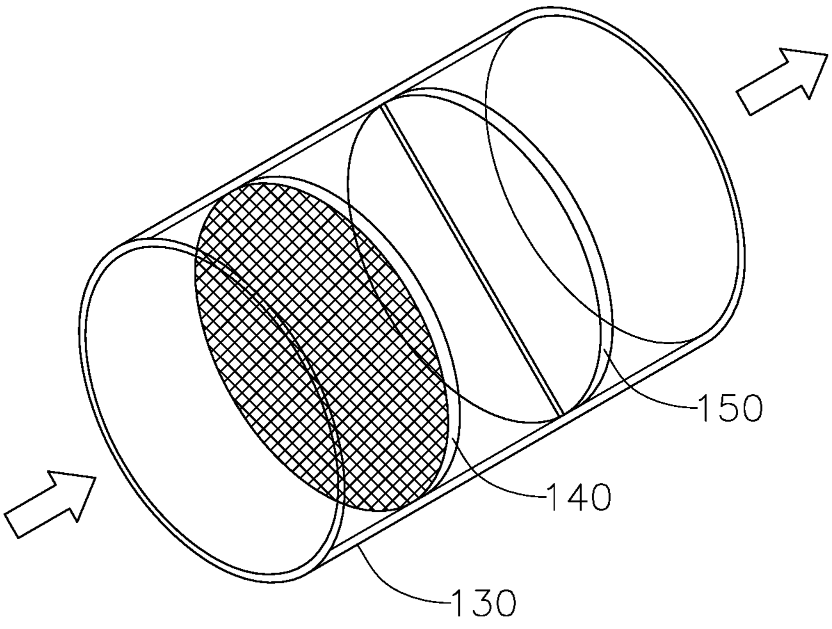
FIG. 3 is a perspective view of a connector having a frangible membrane and a valve according, according to aspects of embodiments of the present disclosure.

In some embodiments of an auto-disable prefillable integrated package of the present disclosure, the integrated package may include 2 chambers that may be configured to contain different drug product components that can be mixed prior to administration of the mixed drug product. Further understanding of such embodiments may be gained by reference to the descriptions of FIGS. 1-3 provided below.

FIG. 1 is a diagram depicting an auto-disable prefillable integrated package 100 having two chambers, according to aspects of embodiments of the present disclosure.

I. Chambers

As depicted in FIG. 1, in some embodiments the integrated package 100 of the present disclosure may contain a first chamber 110 and a second chamber 120. The first chamber 110 and the second chamber 120 may be constructed from any suitable material known to one skilled in the art. As a non-limiting example, the first chamber 110 and the second chamber 120 may be made of any suitable plastic or polymer compound known by one skilled in the art to be safe to use for storage of drug products. In some embodiments, the first chamber 110, the second chamber 120, or both the first chamber 110 and the second chamber 120 may be constructed from a material that allows for the compression of an inner volume of the first chamber 110 and/or second chamber 120. In such embodiments, the use of a plastic or polymer compound that can be flexible or deformable may be used.

In some embodiments, the first chamber 110 and the second chamber 120 may be constructed from the same material. However, in some other embodiments, the first chamber 110 and the second chamber 120 may be constructed from different materials. Likewise, the first chamber 110 and the second chamber 120 may, in some embodiments, have different dimensions, geometries, and other physical properties, such as wall thickness, to meet various user needs. As a non-limiting example, in some embodiments, the first chamber 110 may be smaller in volume than the second chamber 120.

For embodiments where the first chamber 110 and the second chamber 120 may have drug product components that may be mixed before administration, such as with lyophilized drug compounds and reconstitution solutions, the first chamber 110 and the second chamber 120 may be constructed from any suitable plastic or polymer compound that is “see through” or otherwise transparent enough to allow a user to observe the contents of the first chamber 110 and the second chamber 120 before and after mixing.

The first chamber 110 and the second chamber 120 may, in some embodiments, be configured to contain a drug product compound, such as but not limited to, fluid drug products, reconstitution solutions, lyophilized drug products, lyophilized vaccines, binary drug product compounds, and any other solutions that may be administered via injection. Moreover, the first chamber 110 may, in some other embodiments, be configured to contain a different drug product compound or fluid than the second chamber 120. For example, in some embodiments, the first chamber 110 may be configured to contain a fluid while the second chamber 120 is configured to contain a solid compound such as a lyophilized drug compound or vaccine. In some other embodiments, the second chamber 120 may be configured to be a “mixing chamber,” i.e., a chamber intended to have the contents of the first container 110 delivered into and mixed within itself.

II. Connectors, Frangible Membranes, and Valves

In some embodiments of the present disclosure, two or more chambers (e.g., 110 and 120) of the integrated package 100 may be connected by a connector 130 that forms a communicable channel between the two or more chambers (e.g., 110 and 120). Further understanding of embodiments of the connector(s) 130 of the present disclosure, and the additional components such as frangible membranes 140 and valves 150 that may be included within the connector(s) 130, can be had by reference to the descriptions of FIGS. 2-3 provided below.

FIG. 2 is a cross-sectional view of a connector 130 having a frangible membrane 140 and a valve 150, according to aspects of embodiments of the present disclosure.

As depicted, in some embodiments, the connector 130 may have an interior channel that communicably connects the first chamber 110 and the second chamber 120. As will be appreciated by one skilled in the art, the geometry and size of the connector 130 may be varied to meet different user needs, and any suitable geometry and size for the connector 130 as would be known to one skilled in the art is within the scope of the present disclosure. As a non-limiting example, the connector 130 may be a tube or otherwise cylindrical channel between the first chamber 110 and the second chamber 120.

In some embodiments, the connector 130 may include a frangible membrane 140 that may be configured to separate the first chamber 110 and the second chamber 120. In embodiments where the contents of the first chamber 110 are intended to be mixed with the contents of the second chamber 120 prior to administration of the mixed contents, the frangible membrane 140 may be configured to rupture or otherwise break upon the application of a sufficiently large amount of mechanical force provided by a user. The frangible membrane 140 may, in some embodiments, be configured to have a strength that causes the frangible membrane 140 to rupture or otherwise break only once a mechanical force exceeding a "rupture threshold" value is applied. In some embodiments, this rupture threshold value may be varied according to the construction of the frangible membrane 140 including, but not limited to, the material composition of the frangible membrane 140, the thickness and/or dimensions of the frangible membrane 140, and the location of the frangible membrane 140 within the connector 130.

As will be appreciated by one skilled in the art, any suitable material may be used for constructing the frangible membrane 140 within the scope of the present disclosure. This may include, but is not limited to, polyethylene, Teflon®, polypropylene, or other suitable frangible material that may rupture before the device, i.e., the other component parts of the integrated package 100, ruptures. In some embodiments, the frangible membrane 140 may be constructed from an inert material to prevent interaction with the contents of the first chamber 110 and/or second chamber 120. In some other embodiments, the frangible membrane 140 may be constructed from any suitable thermally sealable material.

In some embodiments, the connector 130 of the present disclosure may include a valve 150. As depicted in FIG. 2, in some embodiments, the connector 130 may include both a valve 150 and a frangible membrane 140. As will be appreciated by one skilled in the art, the arrangement of the frangible membrane 140 and the valve 150 in such embodiments may be varied according to user need. As a non-limiting example, in embodiments where the first chamber 110 is configured to contain a fluid and the second chamber 120 is configured to contain a solid, the frangible membrane 140 may be located between the first chamber 110 and the valve 150.

In some embodiments, the valve 150 may serve to prevent backflow of fluid being mixed in one chamber from flowing back into its original chamber. As a non-limiting example, in an embodiment like the one previously described the valve 150 may prevent backflow of the mixed solution from the second chamber 120 back into the first chamber 110. The arrows depicted in FIG. 2 are thus intended to represent the intended direction of fluid flow within an embodiment of the connector 130 having a valve 150. However, the intended direction of fluid flow may be configured according to the configuration of the valve 150 and, as such, the arrows depicted herein are intended to be non-limiting.

In some embodiments, the valve 150 may be a one-way valve. In some other embodiments, the valve 150 may be a disk valve or contain a valve disk. However, any type of valve known by one skilled in the art to be suitable for preventing the backflow of a fluid may be used within the scope of the present disclosure. Additionally, in some other embodiments, the valve 150 may be configured to allow for an aspiration test prior to the administration of the mixed solution.

As will be appreciated by one skilled in the art, in some embodiments the frangible membrane 140 may be integrated with, or otherwise contain, the valve 150.

Turning now to FIG. 3, a perspective view of a connector 130 having a frangible membrane 140 and a valve 150 according, according to aspects of embodiments of the present disclosure, is shown. As described above, in some embodiments, the connector 130 may include the frangible membrane 140 and the valve 150 to allow for a user to keep the contents of the first chamber 110 and the second chamber 120 separated until the contents are to be mixed before administration. In such embodiments, as depicted, the connector 130 may serve to provide a communicable channel that fluid may pass through after the rupture of the frangible membrane 140 and the valve 150 may prevent backflow of the mixed solution from one chamber to another chamber.

The arrows depicted in FIG. 3 are intended to represent the intended direction of fluid flow within an embodiment of the connector 130 having a valve 150. However, the intended direction of fluid flow may be configured according to the configuration of the valve 150 and, as such, the arrows depicted herein are intended to be non-limiting.

III. Hubs, Ports, and Needle Assemblies

Turning back now to FIG. 1, to allow for the injection/administration of the mixed contents of the first chamber 110 and/or second chamber 120, one or more chambers may be configured to be coupled to a hub 160. As will be appreciated by one skilled in the art, the hub 160 may be constructed according to any specification suited for use with any available needle assembly (not shown). The hub 160 may, in some embodiments, be configured to create a location along one of the first chamber 110 or the second chamber 120 that allows for the operable/communicable coupling of a needle assembly (not shown). In some embodiments the hub 160 may include a port 170 that covers all or a portion of the hub 160 prior to the coupling of the needle assembly (not shown). The port 160 may, in some embodiments, isolate the contents or ingredients of the first chamber 110 or the second chamber 120 from the external environment prior to use/administration.

As will be appreciated by one skilled in the art, various different needles may be required to administer different drugs, vaccines, or other compounds. The needles may be hollow, single sided or double sided, and may be any length and gauge as would be known to be useful by one skilled in the art. Likewise, any suitable material known by one skilled in the art for use in needles may be used within the scope of the present disclosure. In some embodiments, the needle may be part of a needle assembly (not shown) that may include a needle shield, one or more components for retracting or otherwise covering the needle after administration, and a connection portion or threaded portion for coupling to the hub 160.

IV. Bonded Periphery

As depicted in the FIG. 1, in some embodiments, the integrated package 100 may include a bonded periphery 180. In such embodiments, the bonded periphery 180 may be made of any suitable material. In some embodiments, the bonded periphery 180 may be made of the same material or compound as the first chamber 110 and/or the second chamber 120. The bonded periphery 180 may, in some embodiments, include the outer boundary of the integrated package 100 where a top half of the integrated package 100 and a lower half of the integrated package 100 are bonded, thermally or otherwise, during construction/filling of the integrated package. For simplicity, the top half of the integrated package 100 and the lower half of the integrated package 100 are not depicted separately. As will be appreciated by one skilled in the art, any suitable size and geometry for the bonded periphery 180 may be used within the scope of the present disclosure.

Multi-Chamber Integrated Package

In some embodiments of a multi-chamber prefillable integrated package of the present disclosure, the multi-chamber integrated package may include 3 or more chambers that may be configured to contain different drug product components that can be mixed prior to administration of the mixed drug product. Further understanding of such embodiments may be gained by reference to the descriptions of FIG. 4 provided below.

Figure 4:
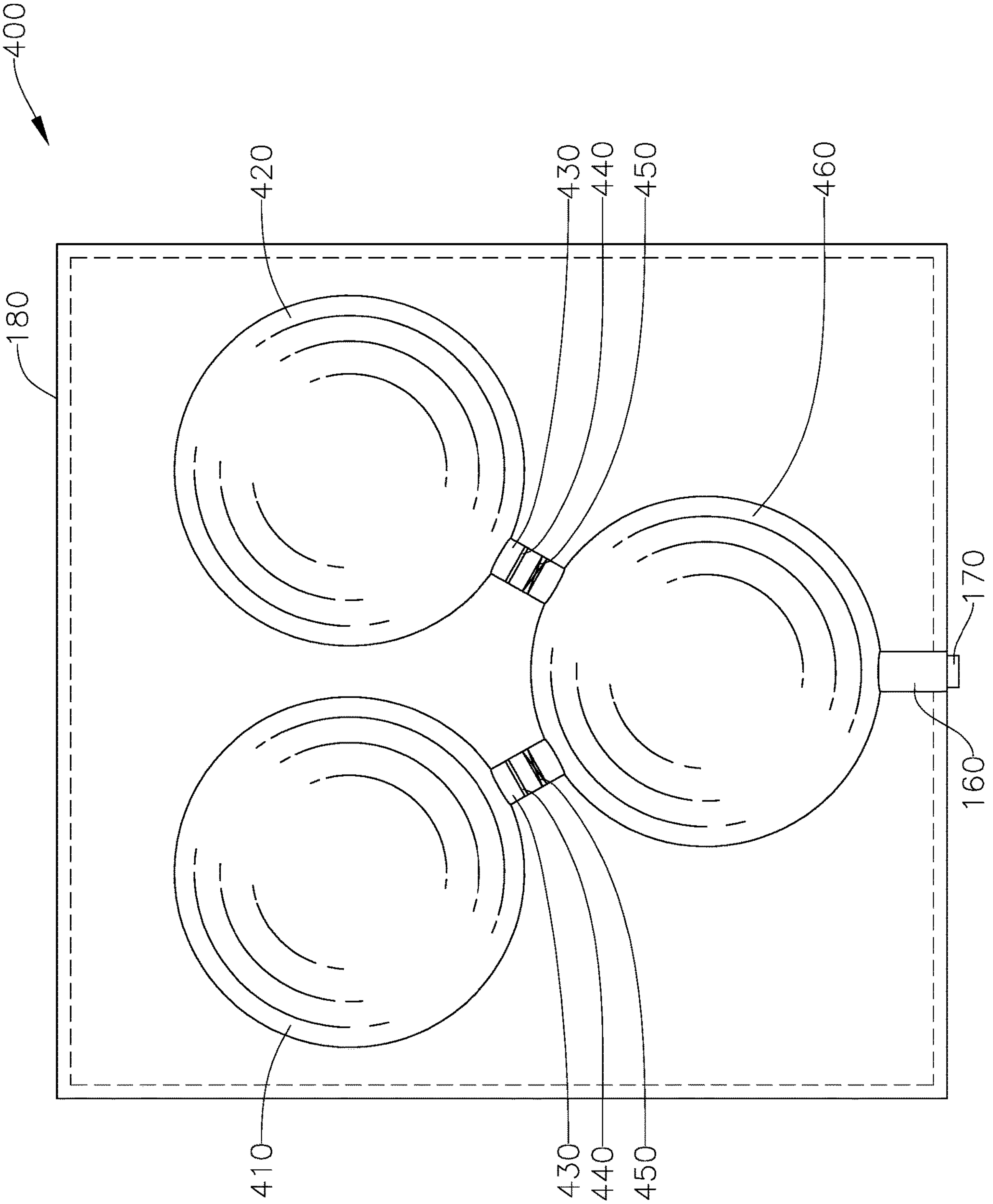
FIG. 4 is a diagram depicting a multi-chamber integrated package having 3 chambers, according to aspects of embodiments of the present disclosure.

FIG. 4 is a diagram depicting a multi-chamber integrated package 400 having 3 chambers, according to aspects of embodiments of the present disclosure.

As will be appreciated by one skilled in the art, the disclosures provided above for the component parts/features of the 2-chamber embodiment of the integrated package 100 shown in FIG. 1 may be applicable to any of the similar component parts/features of the multi-chamber integrated package 400 depicted in FIG. 4. As depicted, where more than two chambers, e.g., first chamber 410, second chamber 420, and third chamber 460, are included within the multi-chamber integrated package 400, more than one connector 430 may be used to connect any pair of chambers. As previously described, the one or more connectors 430 may, in some embodiments, include the frangible membrane 440 and/or the valve 450.

Furthermore, as will be appreciated by one skilled in the art, the size, geometry, and arrangement of the chambers and corresponding connectors 430 may be varied to any suitable configuration. For example, as depicted, in some embodiments the first chamber 410 and the second chamber 420 may each be independently communicably connected to a third chamber 460 by their respective connectors 430. However, in some other embodiments, a first chamber may be configured to be communicably connected by a first connector to a second chamber which is then communicably connected by a second connector to a third chamber. In such embodiments, the final chamber, i.e., third chamber, may be configured to be mixed in and may be coupled to the hub 160.

Syringe-Type Integrated Package

In some embodiments of a syringe-type prefillable integrated package of the present disclosure, the syringe-type integrated package may include 2 chambers that may be configured to contain different drug product components that can be mixed prior to administration of the mixed drug product. Further understanding of such embodiments may be gained by reference to the descriptions of FIG. 5 provided below.

Figure 5:
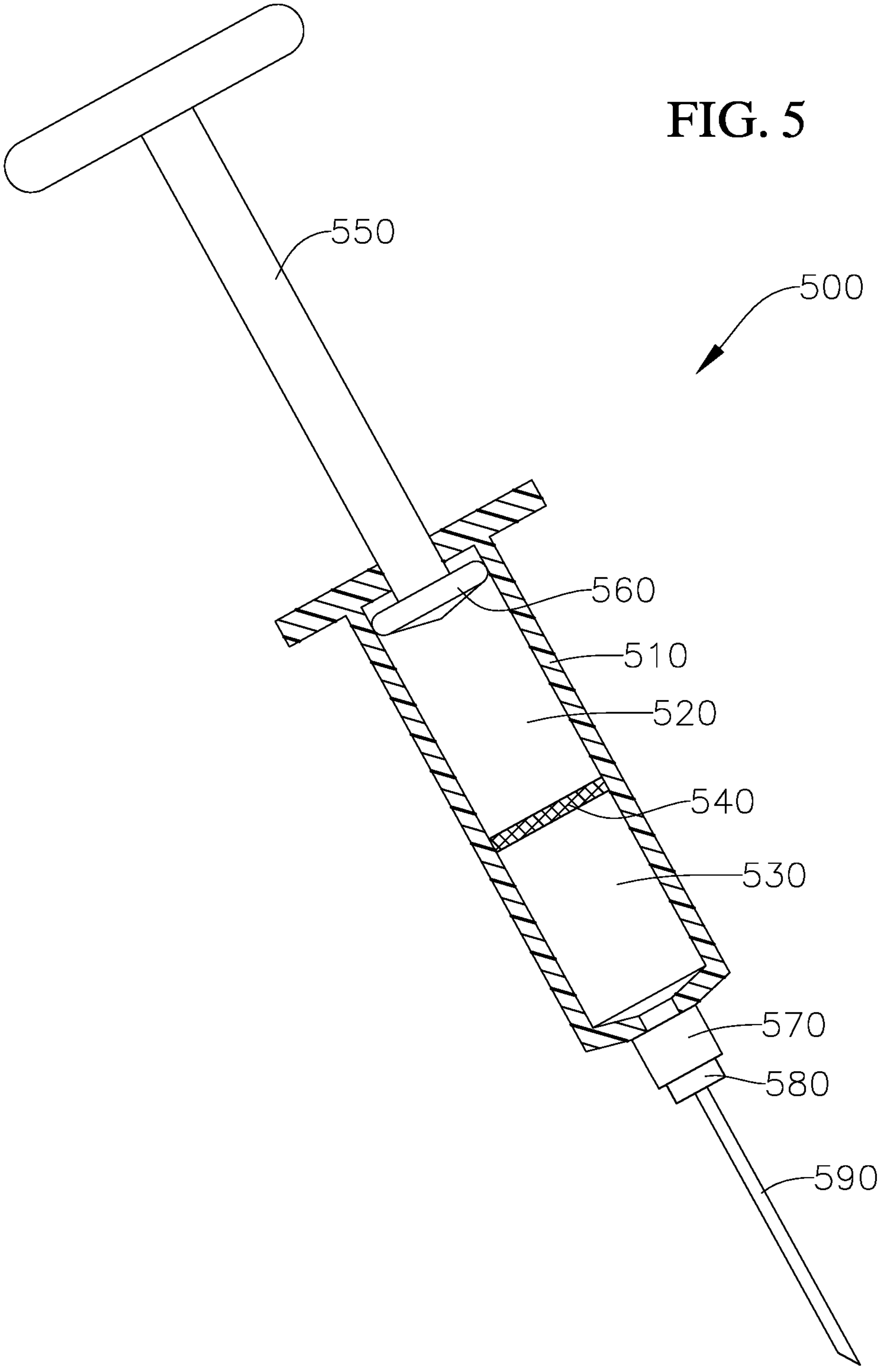
FIG. 5 is a diagram depicting a syringe-type integrated package having 2 chambers, according to aspects of embodiments of the present disclosure.

FIG. 5 is a diagram depicting a syringe-type integrated package 500 having 2 chambers, a first chamber 520 and a second chamber 530, according to aspects of embodiments of the present disclosure.

I. Cylindrical Body Having 2 Chambers Separated by A Frangible Membrane

As depicted, some embodiments of the syringe-type integrated package 500 of the present disclosure may include a cylindrical body 510. As will be appreciated by one skilled in the art, any suitable material may be used to construct the cylindrical body 510, including, but not limited to, those materials described above as being suitable for the integrated package 100 embodiment depicted in FIG. 1. Likewise, any suitable size and or geometry may be used for the cylindrical body 510.

An internal volume of the cylindrical body 510 may be divided into two or more chamber by one or more frangible membranes 540. As depicted, in some embodiments, the cylindrical body 510 may contain a first chamber 520 and a second chamber 530 separated by the frangible membrane 540. As will be appreciated by one skilled in the art, the syringe-type integrated package 500 may, in some embodiments, have the first chamber 520 and the second chamber 530 configured to contain different contents. In some embodiments, the first chamber 520 may be configured to contain a fluid, such as but not limited to a reconstitution fluid. Likewise, in some other embodiments, the second chamber 530 may be configured to hold a solid compound, such as a lyophilized drug or vaccine.

The frangible membrane 540 may, in some embodiments, be ruptured prior to administration to allow for the mixing of the contents of the first chamber 520 and the second chamber 530. In such embodiments, the frangible membrane 540 may be configured to rupture when a sufficiently large pressure is created within the first chamber 520.

II. Plunger Assembly

In some embodiments of the syringe-type integrated package 500 of the present disclosure, the rupture of the frangible membrane 540 may be caused by the build up of pressure within the first chamber 520 as a user applies a mechanical force to a plunger assembly 550 forcing it into the volume of the cylindrical body 510. As will be understood by one skilled in the art, any suitable size, geometry, and materials as are known to be suitable for use in a plunger assembly 550 of a syringe may be used within the scope of the present disclosure. In some embodiments, the plunger assembly 550 may include one or more rubberized gaskets 560.

Once the plunger assembly 550 has been pressed into the cylindrical body 510 with enough force to rupture the frangible membrane 540, the contents of the first chamber 520 and the second chamber 530 may be mixed in the now communicably connected first chamber 520 and second chamber 530. Afterward, once the solution has been mixed, the plunger assembly 550 may be further pressed into the internal volume of the cylindrical body 510 to force the mixed contents out of the cylindrical body 510 through a needle assembly 590 operably coupled to a hub 570 coupled to an end of the cylindrical body 510 opposite of the plunger assembly 550. As will be appreciated by one skilled in the art, the disclosures provided above regarding the hub 160, port 170, and needle assembly (not shown) of the prior described embodiments of FIG. 1 are relevant and applicable to the syringe-type embodiments described herein, e.g., the hub 570, port 580, and needle assembly 590 of FIG. 5.

It will be understood that embodiments described herein should be considered in a descriptive sense only and not for purposes of limitation. Descriptions of features or aspects within each exemplary embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope as defined by the following claim. It should be noted that although examples of the invention are set forth herein, the claims, and the full scope of any equivalents, are what define the metes and bounds of the invention.

What is claimed is:

1. An auto-disable prefillable integrated package apparatus, comprising:

a top half having a top boundary geometry; and a lower half having a lower boundary geometry similar to the top boundary geometry and configured to couple to the top half;

wherein the top half and the lower half are configured such that the top half and the lower half when coupled form the auto-disable prefillable integrated package comprising;

a first chamber;

a second chamber;

a connector configured to form a communicable channel between the first chamber and the second chamber;

a frangible membrane configured to form a rupturable barrier within the connector that separates the first chamber and the second chamber;

a hub configured to be communicably coupled to the second chamber; and a bonded periphery coupled to the hub and surrounding the first chamber and the second chamber;

wherein the bonded periphery forms an outer boundary of the auto-disable prefillable integrated package along a perimeter of the auto-disable prefillable integrated package defined by the top boundary geometry coupled to the lower boundary geometry.

2. The auto-disable prefillable integrated package apparatus of claim 1, wherein the second chamber comprises a compressible inner volume.

3. The auto-disable prefillable integrated package apparatus of claim 1, further comprising a valve configured to prevent fluid flow from the second chamber into the first chamber via the connector.

4. The auto-disable prefillable integrated package apparatus of claim 3, wherein the valve comprises a disc valve.

5. The auto-disable prefillable integrated package apparatus of claim 1, further comprising a needle assembly configured to be communicatively coupled to the hub.

6. The auto-disable prefillable integrated package apparatus of claim 1, wherein the outer boundary of the auto-disable prefillable integrated package apparatus is configured in a rectangular geometry.

7. The auto-disable prefillable integrated package apparatus of claim 1, wherein the frangible membrane is configured to rupture when a mechanical force above a rupture threshold is applied by a user to the connector.

8. The auto-disable prefillable integrated package apparatus of claim 1, wherein the hub comprises a port.

9. The auto-disable prefillable integrated package apparatus of claim 1, wherein the frangible membrane comprises a polymer compound.

* * * * *